United States Patent [19]

Estermann et al.

[11] Patent Number: 5,338,730
[45] Date of Patent: Aug. 16, 1994

[54] USE OF THE (R) ISOMER OF 2-[(2-OCTA-DECYLOXYMETHYL-TETRAHYDRO-2-FURANYLMETHOXY)-HYDROXYPHOSPHINYLOXY]-N,N,N-TRIMETHYLETHANAMINIUM HYDROXIDE INNER SALT-4-OXIDE IN TREATING MULTIPLE SCLEROSIS

[75] Inventors: Heinrich Estermann, Allschwil, Switzerland; Prasad K. Kapa, Parsippany, N.J.; Russell L. Underwood, Randolph, N.J.; William J. Houlihan, Mountain Lakes, N.J.

[73] Assignee: Sandoz Ltd., Basle, Switzerland

[21] Appl. No.: 73,215

[22] Filed: Jun. 4, 1993

Related U.S. Application Data

[60] Division of Ser. No. 692,094, Apr. 26, 1991, Pat. No. 5,229,377, which is a continuation-in-part of Ser. No. 647,396, Jan. 29, 1991, abandoned, which is a continuation-in-part of Ser. No. 540,438, Jun. 19, 1990, abandoned.

[51] Int. Cl.$^5$ .................. A61K 31/665; C07F 9/141
[52] U.S. Cl. ...................................... 514/99; 514/903; 549/218
[58] Field of Search .................. 514/903, 99; A61K 31/665

[56] References Cited

U.S. PATENT DOCUMENTS 4,601,987  7/1986  Klibanov et al. .................. 514/99
4,673,672  6/1987  Houlihan et al. .................. 514/99

OTHER PUBLICATIONS

*Chemistry Letters*, pp. 1717–1720 (1988).
*Biotechnology*, vol. 7A, p. 113 (1987).
*Tetrahedron Letters*, vol. 31, No. 4, pp. 445–448 (1990).
*Tetrahedron*, vol. 42, No. 13, pp. 3351–3403 (1986).

*Primary Examiner*—Cecilia Tsang
*Attorney, Agent, or Firm*—Robert S. Honor; Melvyn M. Kassenoff; Joseph J. Borovian

[57] ABSTRACT

A process for preparing the (R) stereoisomer of 2,2-bis(-hydroxmethyl)-tetrahydrofuran monobutyrate comprising subjecting the dibutyric ester of the 2,2-bis(hydroxymethyl)-tetrahydrofuran to enzymatic hydrolysis. The invention also relates to the novel (R) stereoisomer prepared by the instant process and to its more stable forms. In addition, the invention relates to the use of the (R) stereoisomer in preparing stereoisomers of pharmacologically active compounds and to certain specific stereoisomers produced thereby.

5 Claims, No Drawings

USE OF THE (R) ISOMER OF 2-[(2-OCTA-DECYLOXYMETHYL-TETRAHYDRO-2-FURANYLMETHOXY)-HYDROXYPHOS-PHINYLOXY]-N,N,N-TRIMETHYLE-THANAMINIUM HYDROXIDE INNER SALT-4-OXIDE IN TREATING MULTIPLE SCLEROSIS

This is a division of application Ser. No. 07/692,094, filed Apr. 26, 1991, now issued as U.S. Pat. No. 5,229,377 which in turn is a continuation-in-part of application Ser. No. 07/647,396, filed Jan. 29, 1991, which in turn is a continuation-in-part of application Ser. No. 07/540,438, filed Jun. 19, 1990, the latter two of which are now abandoned.

The present invention relates to a process for preparing the (R) stereoisomer of 2,2-bis(hydroxymethyl)-tetrahydrofuran, monobutyrate comprising subjecting the dibutyric ester of 2,2-bis(hydroxymethyl)-tetrahydrofuran to enzymatic hydrolysis. In addition, the present invention relates to the use of said isomer in preparing stereoisomers of pharmacologically active compounds, and to certain specific stereoisomers produced thereby.

As is well known, many pharmacologically active compounds occur as a mixture of stereoisomers. Moreover, despite the fact that the desired pharmacological activity usually resides in one stereoisomer, mixtures of stereoisomers are employed because the prohibitive cost of separation of the stereoisomers exceeds the potential advantage of a possible increase in activity. However, it is quite apparent that many pharmacologists are becoming increasingly aware of other implications in the administration of mixtures of stereoisomers wherein one or more stereoisomers have to be regarded as impurities which may not only be devoid of the desired therapeutic effect but, more importantly, may contribute unwanted physiological effects including toxicity.

Numerous research endeavors have been directed to processes for producing specific stereoisomers of pharmacologically active compounds, and such processes are well documented in the patent and non-patent literature. Prominent among these processes is the use of enzymes to induce stereospecific transformations. For example, in Chemistry Letters, pgs. 1717–1720 (1988), there is described the enzyme-catalyzed asymmetrization of cis-2,5-bis(hydroxymethyl)-tetrahydrofurans. More particularly, this reference describes the asymmetric hydrolysis of various diesters of cis-2,5-bis(hydroxymethyl)-tetrahydrofuran catalyzed by PLE (pig liver esterase), PPL (porcine pancreas lipase) or CCL (Candida cylindracea lipase). As can be seen from the results obtained, the yields are rather low with the exception of one particular case, viz., Entry 1 in Table 1, where an 86% yield was obtained. In connection with certain anti-tumor compounds disclosed in U.S. Pat. No. 4,673,672, it was desired to obtain the optically pure intermediates derived from 2,2-bis(hydroxymethyl)-tetrahydrofuran. As the enzymatic processes are, in general, substrate specific, there was a need to develop suitable methodology independents for the as asymmetrization of 2,2-disubstituted tetrahydrofuran derivatives. In contrast to the 2,5-system, the optically pure monoacetates derived from the 2,2-system are prone to racemization via the intramolecular acyl transfer. To this end, the instant invention represents a simple and economic process for preparing a specific stereoisomer in good yields utilizing relatively small amounts of enzyme and mild reaction conditions, which stereoisomer is a valuable intermediate in the preparation of specific stereoisomers of pharmacologically active compounds.

In accordance with the process of the instant invention, the (R) stereoisomer of 2,2-bis(hydroxymethyl)-tetrahydrofuran, monobutyrate of formula I

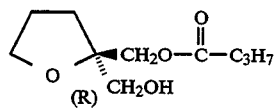

is prepared by adding an enzyme to a buffered suspension of 2,2-bis(hydroxymethyl)-tetrahydrofuran, dibutyrate of formula II

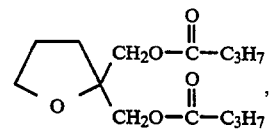

the amount of enzyme added being between 1 and 40 mg per mmol of the dibutyric ester.

As to the enzymes employed in the process of the instant invention, a suitable enzyme is the lipase PPL (porcine pancreas) or a microbial lipase selected from LCL (candida lipolytica), LMJ (mucor javanicus) and LPF (pseudomonas fluorescence), all of which are known and commercially available. Preferred enzymes are PPL, LMJ and LPF.

The enzyme is added to a buffered aqueous suspension of the dibutyric ester of formula II, the pH of which has been adjusted to 7 (with either acetic acid or dilute sodium hydroxide). Preferably, the enzyme is added to a buffered suspension of the dibutyric ester in a cosolvent mixture, which mixture comprises water and a n-$C_5$-$C_7$ aliphatic hydrocarbon, i.e., pentane, hexane or heptane, in a 1:1 ratio, with the pH of the suspension having been adjusted to 7 prior to the addition of the enzyme.

Alternatively, the dibutyric ester of formula II is added to a buffered aqueous suspension of the enzyme, the pH of which has been adjusted to 7 (with either acetic acid or dilute sodium hydroxide). Preferably, the dibutyric ester is added to a buffered suspension of the enzyme in a cosolvent mixture, which mixture comprises water and a n-$C_5$-$C_7$ aliphatic hydrocarbon, i.e., pentane, hexane or heptane, in a 1:1 ratio, with the pH of the suspension having been adjusted to 7 prior to the addition of the dibutyric ester.

The preparation of the (R) stereoisomer of 2,2-bis-(hydroxymethyl)-tetrahydrofuran, monobutyrate is conducted at a temperature of from 0° to 300° C. for a period of between 15 minutes and 3 hours, preferably between 30 minutes and 2 hours, more preferably between 30 minutes and 1 hour.

The resultant (R) stereoisomer of 2,2-bis(hydroxymethyl)-tetrahydrofuran, monobutyrate may be purified by conventional techniques such as column chromatography, preparative thin layer chromatography or fractional distillation.

The 2,2-bis(hydroxymethyl)-tetrahydrofuran dibutyric ester which is employed in the instant process may be prepared by methods described in the literature. For example, the dibutyric ester may be prepared as follows:

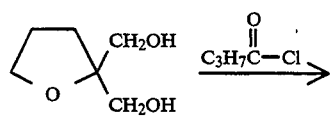

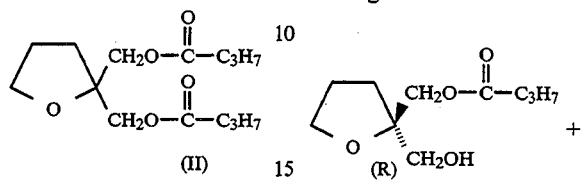

In the above reaction, 2,2-bis(hydroxymethyl)-tetrahydrofuran is reacted with a slight excess of 2 moles of butyryl chloride to yield the dibutyric ester of formula II. The reaction is conveniently carried out in the presence of an inert, organic solvent, e.g., a chlorinated aliphatic hydrocarbon such as methylene chloride, or an aromatic hydrocarbon such as benzene or toluene, at a temperature of between 10° and 40° C. for a period of between 4 and 12 hours. The resultant dibutyric ester may be purified by conventional techniques, such as fractional distillation.

The (R) stereoisomer of 2,2-bis(hydroxymethyl)-tetrahydrofuran, monobutyrate of formula II is a novel compound and, as such, also forms a part of this invention. It is preferred, however, because of its limited stability to convert the (R) stereoisomer of 2,2-bis(hydroxymethyl)-tetrahydrofuran, monobutyrate to a more stable form. For example, the monobutyric ester may be converted to a silylated form in accordance with the following reaction scheme:

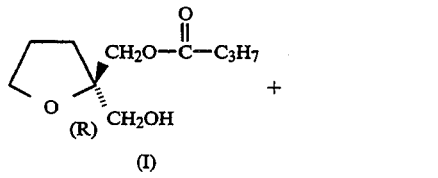

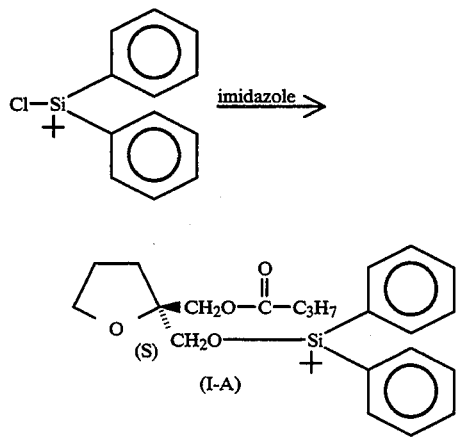

In the above reaction, the (R) stereoisomer of 2,2-bis(-hydroxymethyl)-tetrahydrofuran, monobutyrate, preferably in crude form, is reacted with t-butylchlorodiphenyl silane in the presence of 2 equivalents of imidazole to yield the (S) stereoisomer of the silyl ether of formula I-A. The silylation is conveniently carried out in a polar, aprotic solvent, e.g., a dialkylamide such as dimethylformamide or dimethylacetamide, or a lower alkyl nitrile such as acetonitrile, at a temperature of between 0° and 30° C. for a period of between 2 and 24 hours.

Alternatively, the monobutyric ester may be converted to a tritylated form in accordance with the following reaction scheme:

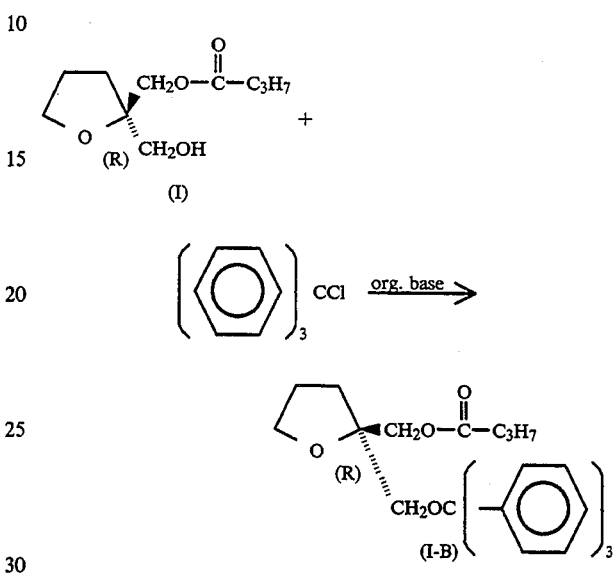

In the above reaction, the (R) stereoisomer of 2,2-bis(hydroxymethyl)-tetrahydrofuran, monobutyrate, preferably in crude form, is reacted with triphenylchloromethane in the presence of an organic base such as triethylamine or pyridine to yield the (R) stereoisomer of the trityl ether of formula I-B. The tritylation is conveniently carried out in an inert, organic solvent, e.g., a chlorinated, aliphatic hydrocarbon such as methylene chloride, at a temperature of from −30° to 30° C. for a period of between 30 minutes and 24 hours.

In either case, i.e., regardless of whether the silylated or tritylated form is prepared, the resultant (S) or (R) stereoisomers may be purified by conventional techniques.

The (S) and (R) stereoisomers of formulae I-A and I-B are novel compounds and, as such, also form a part of this invention.

The (R) stereoisomer of 2,2-bis(hydroxymethyl)-tetrahydrofuran, monobutyrate of formula I, and its more stable forms, i.e., the (S) stereoisomer of the silyl ether of formula I-A and the (R) stereoisomer of the trityl ether of formula I-B, are valuable intermediates in the preparation of specific stereoisomers of pharmacologically active compounds. For example, they are valuable intermediates in the preparation of specific stereoisomers of certain anti-tumor compounds disclosed in U.S. Pat. No. 4,673,672.

More particularly, and with respect to the specific compound of Example 5 of said U.S. patent for purposes of illustration, it can be seen that said compound contains an asymmetric carbon atom and, therefore, the compound depicted is a mixture of two stereoisomers, viz., the (R) and (S) isomers. By employing the novel (S) stereoisomer of the silyl ether of formula I-A as the starting material, the (S) stereoisomer of the compound of Example 5 may be prepared as depicted below:

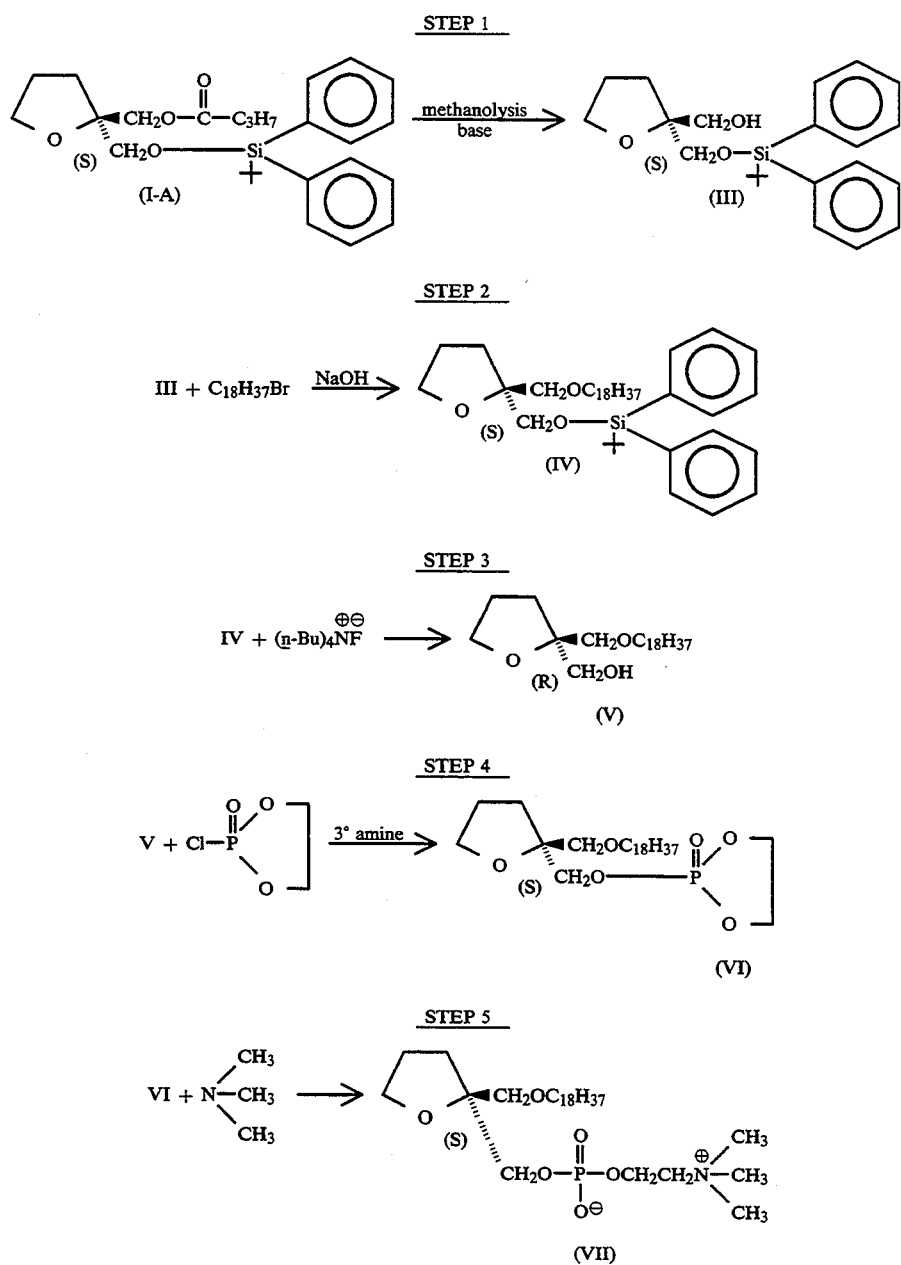

With respect to the individual steps, Step 1 concerns the methanolysis of the (S) stereoisomer of the silyl ether of formula I-A in the presence of an organic base such as triethylamine or pyridine, or an inorganic base such as sodium or potassium carbonate to yield the (S) isomer of the compound of formula III. The methanolysis is carried out at a temperature of from 0° to 30° C. for a period of between 30 minutes and 16 hours.

Step 2 involves the alkylation of the (S) isomer of the compound of formula III with 1-bromooctadecane in the presence of sodium hydroxide to yield the (S) isomer of the compound of formula IV. The alkylation is conducted under the identical reaction conditions set forth in Step A of U.S. Pat. No. 4,673,672.

Step 3 involves the reaction of the (S) isomer of the compound of formula IV with tetrabutylammonium fluoride to yield the (R) isomer of the compound of formula V. This reaction is conveniently carried out in the presence of an inert, organic solvent, e.g., a cyclic ether such as tetrahydrofuran, or a lower alkyl nitrile such as acetonitrile, at a temperature of from 0° to 30° C. for a period of between 2 and 5 hours.

As to Step 4 and Step 5 for preparing the (S) isomer of the compound of formula VI and the (S) isomer of the compound of formula VII, respectively, they are conducted under the identical reaction conditions set forth in Step 7A and Step 8 of U.S. Pat. No. 4,673,672.

The (R) isomer of the compound of Example 5 of U.S. Pat. No. 4,673,672 may be prepared essentially as follows employing the (S) isomer of the compound of formula III as the starting material:

STEP A

-continued

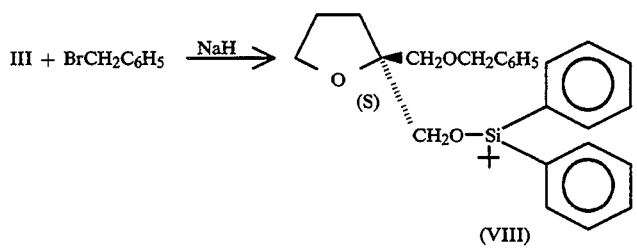

STEP B

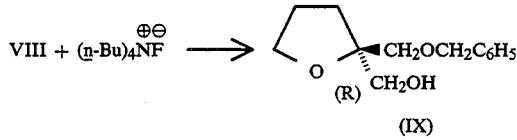

STEP C

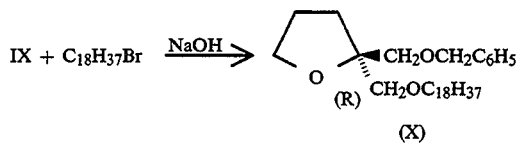

STEP D

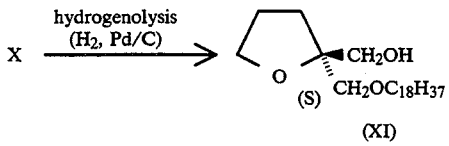

STEP E

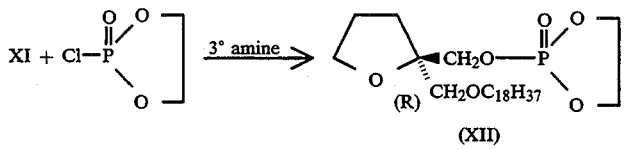

STEP F

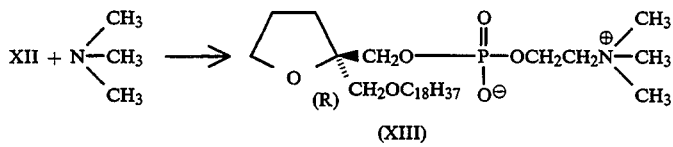

With regard to the steps individually, Step A concerns the reaction of the (S) isomer of the compound of formula III with benzyl bromide in the presence of sodium hydride to yield the (S) isomer of the compound of formula VIII. This reaction is conveniently carried out in an inert, organic solvent, e.g., a cyclic ether such as tetrahydrofuran, at a temperature of between 0° and 60° C. for a period of between 30 minutes and 24 hours.

Step B involves the reaction of the (S) isomer of the compound of formula VIII with tetrabutylammonium fluoride to yield the (R) isomer of the compound of formula IX. As to reaction conditions, i.e., solvents, reaction temperatures and reaction times, they are analogous to that described above in Step 3.

Step C is directed to the alkylation of the (R) isomer of the compound of formula IX with 1-bromooctadecane in the presence of sodium hydroxide to yield the (R) isomer of the compound of formula X. The alkylation is conducted under the identical reaction conditions set forth in Step A of U.S. Pat. No. 4,673,672.

Step D involves the hydrogenolysis of the benzyl ether group of the (R) isomer of the compound of formula X by dissolving said compound in a lower alkanol, e.g., methanol, ethanol and the like, or a mixture of a lower alkanol and water (up to 15%), with palladium on carbon and subjecting the resultant mixture to a pressure of 15 and 65 lbs. of hydrogen gas at a temperature of from 20° to 50° C. for a period of between 5 and 20 hours to yield the (S) isomer of the compound of formula XI.

As to Step E and Step F for preparing the (R) isomer of the compound of formula XII and the (R) isomer of the compound of formula XIII, respectively, they are conducted under the identical reaction conditions set forth in Step 7A and Step 8 of U.S. Pat. No. 4,673,672.

More conveniently, the (S) stereoisomer of the compound of Example 5 may be prepared as follows employing the novel (R) stereoisomer of the trityl ether of formula I-B as the starting material:

REACTION A

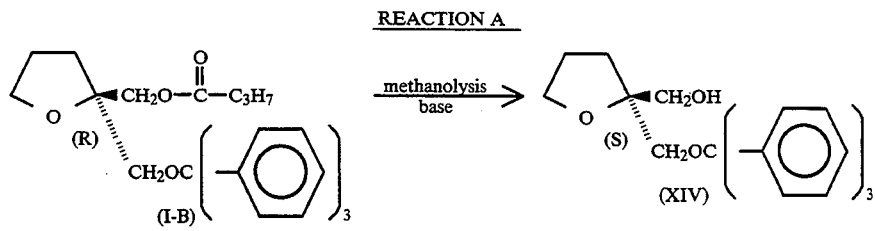

REACTION B

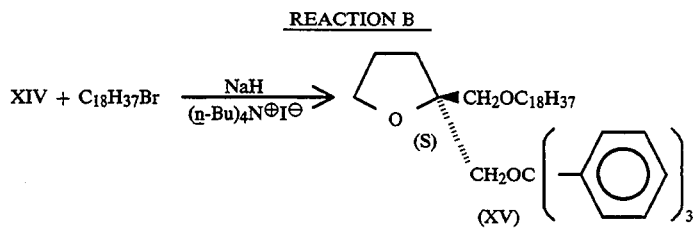

REACTION C

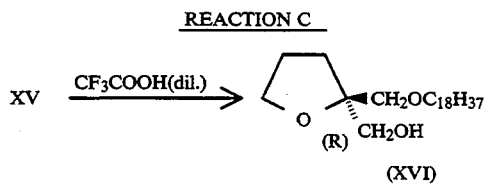

REACTION D

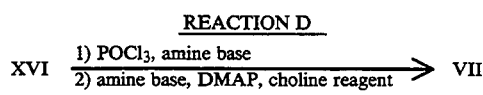

With respect to the individual reactions, Reaction A concerns the methanolysis of the (R) stereoisomer of the trityl ether of formula I-B in the presence of an organic base such as triethylamine or pyridine, or an inorganic base such as sodium or potassium carbonate, to yield the (S) isomer of the compound of formula XIV. As to reaction times and temperatures, the methanolysis is carried out analogously to that set forth above in Step 1.

Reaction B involves the alkylation of the (S) isomer of the compound of formula XIV with 1-bromooctadecane in the presence of sodium hydride (60% dispersion) and tetrabutylammonium iodide to yield the (S) isomer of the compound of formula XV. The reaction is conveniently carried out in the presence of an inert, organic solvent, e.g., a cyclic ether such as tetrahydrofuran, at a temperature of from 0° to the reflux temperature of the solvent for a period of between 5 and 16 hours.

Reaction C involves the reaction of the (S) isomer of the compound of formula XV with an aqueous solution of trifluoroacetic acid to yield the (R) isomer of the compound of formula XVI. The reaction may conveniently be carried out in the presence of an inert, organic solvent, e.g., a halogenated hydrocarbon such as methylene chloride, at a temperature of from 0° to 40° C. for a period of between 30 minutes and 16 hours.

The first step of Reaction D involves the reaction of the (R) isomer of the compound of formula XVI with phosphorus oxychloride in the presence of an amine base such as pyridine or triethylamine. The reaction is conveniently carried out in the presence of an inert, organic solvent, e.g., a halogenated hydrocarbon such as methylene chloride, at a temperature of from 0° to 40° C. for a period of between 6 and 24 hours.

The second step of Reaction D involves the reaction of the product produced in the first step with Choline reagent (i.e., ethanaminium, 2-hydroxy,N,N,N-trimethyl-4-methylbenzenesulfonate) in the presence of an amine base such as pyridine or triethylamine and a catalytic amount of 4-dimethylaminopyridine to yield the (S) isomer of the compound of formula VII. The reaction is conveniently carried out at a temperature of from 10° to 40° C. for a period of between 16 hours and 4 days.

Similarly, at the (R) stereoisomer of the compound of Example 5 may be more conveniently prepared as set forth below employing the (S) isomer of the compound of formula XIV as the starting material:

STEP AA

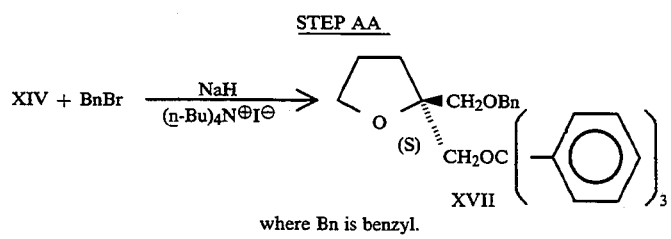

where Bn is benzyl.

STEP BB

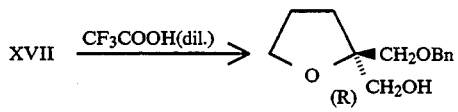

where Bn is as defined above.

STEP CC

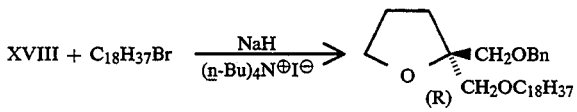

where Bn is as defined above.

STEP DD

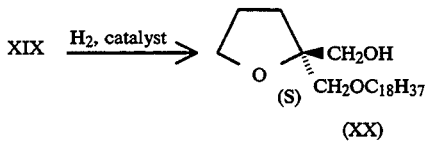

STEP EE

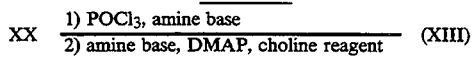

With regard to the individual steps, Step AA involves the reaction of the (S) isomer of the compound of formula XIV with benzyl bromide in the presence of sodium hydride (60% dispersion) and tetrabutylammonium iodide to yield the (S) isomer of the compound of formula XVII. The reaction is conveniently carried out in the presence of an inert, organic solvent, e.g., a cyclic ether such as tetrahydrofuran, at a temperature of from 0° C. to the reflux temperature of the solvent for a period of between 2 and 5 hours.

Step BB involves the reaction of the (S) isomer of the compound of formula XVII with an aqueous solution of trifluoroacetic acid to yield the (R) isomer of the compound of formula XVIII. As to solvents, reaction temperatures and reaction times, they are analogous to that described above in Reaction C.

Step CC involves the alkylation of the (R) isomer of the compound of formula XVIII with 1-bromooctadecane in the presence of sodium hydride (60% dispersion) and tetrabutyl ammonium iodide to yield the (R) isomer of the compound of formula XIX. As to solvents, reaction temperatures and reaction times, they are analogous to that described above in Reaction B.

Step DD involves the hydrogenolysis of the benzyl ether group of the (R) isomer of the compound of formula XIX by dissolving said compound in a lower alkanol such as methanol or ethanol, and adding the solution to palladium on carbon in the presence of a trace amount of acetic acid. The resultant mixture is then subjected to a pressure of between 15 and 65 lbs. of hydrogen gas at a temperature of from 20° to 50° C. for a period of between 5 and 20 hours to yield the (S) isomer of the compound of formula XX.

As to Step EE for preparing the (R) isomer of the compound of formula XIII, the solvents, reaction temperatures and reaction times for both of the reactions are analogous to that set forth above in Reaction D.

With regard to the two stereoisomers of Example 5 of U.S. Pat. No. 4,673,672, they appear to exhibit a unique and surprising pharmacological profile and, as a result, the (R) and (S) isomers, per se, and their individual uses, represent additional aspects of this invention. More particularly, it has been discovered that the specific isomer prepared in Step F or Step EE, i.e., the (R) isomer of formula XIII, is more effective than the racemic mixture, i.e., the compound of Example 5 of U.S. Pat. No. 4,673,672, in treating multiple sclerosis, whereas the corresponding (S) isomer prepared in Step 5 or Reaction D, i.e., the compound of formula VII, appears to be ineffective in treating multiple sclerosis. The usefulness of the (R) isomer of formula XIII in treating multiple sclerosis can be demonstrated employing the following test methods:

Experimentally Induced Allergic Encephalomyelitis (EAE) in the Rat

[Levine et al., AM. J. PATH. 47 (1965) 61; McFarlin et al, J. IMMUNOL. 113 (1974) 712; Borel, TRANSPLANT & CLIN. IMMUNOL. 13) (1981) 3].

Male Wistar rats are injected in the hind paws with 0.1 ml. of a mixture of bovine spinal cord and complete Freund's adjuvant. The test compound is administered at dosages of from 5 to 50 mg/kg/day p.o. 5 days a week, commencing on the day of sensitization and continuing for 3 weeks. Onset of EAE in control groups receiving no medication generally commences between 9 to 16 days after sensitization and is marked by symptoms of paralysis in the hind limbs and tail. Test animals are examined daily for symptoms of the disease and disease occurrence is scored as positive when complete involvement of both hind legs and tail is observed. The test animals are kept under observation for a total period of 25 days.

On administration of the (R) isomer of formula XIII at the above-indicated dosage rates, a substantial reduction of occurrence is observed over the test period in comparison with occurrence in control groups receiving placebo.

Established Experimental Allergic Encephalomyelitis (EEAE)

Testing is carried out analogously to that described above with the exception that the administration of the test compound commences on day 8 to day 9 after sensitization (i.e., immediately prior to appearance of disease symptoms) at dosages of from 5 to 50 mg/kg/day p.o. either daily or every second day and continuing for 2 weeks. During the testing period, the animals are examined daily for symptoms of the disease and scored as in the above test method.

On administration of the (R) isomer of formula XIII at the above dosage rates, a substantial reduction of appearance of EAE disease symptoms is observed over the test period in comparison with appearance in control groups receiving placebo.

The precise dosage of the (R) isomer of formula XIII to be employed in treating multiple sclerosis depends upon several factors including the host, the nature and the severity of the condition being treated and the mode of administration. However, in general, satisfactory inhibition of the symptoms of multiple sclerosis is achieved when the (R) isomer of formula XIII is administered orally at a daily dosage of between 0.5 and 30 mg/kg body weight, preferably between 1 and 20 mg/kg, or for most larger primates, at a total daily dosage of between 100 and 600 mg. A preferred total daily dosage for most larger primates is between 100 and 300 mg.

Usually, a small dosage is administered initially and the dosage is gradually increased until the optimal dosage for the host under treatment is determined. The upper limit of dosage is that imposed by side effects, and can be determined by trial for the host being treated, including humans.

As indicated above, a preferred total daily dosage for most larger primates, e.g., humans, is 100 to 300 mg. However, it should be understood that when a clear improvement in the symptoms of multiple sclerosis is observed upon daily administration of between 100 and 300 mg of the (R) isomer of formula XIII, the dosage regimen can be decreased to between 100 and 300 mg of the (R) isomer of formula XIII every second day.

The (R) isomer of formula XIII may be combined with one or more pharmaceutically acceptable carriers and, optionally, one or more conventional pharmaceutical adjuvants and administered orally in the form of tablets, dispersible powders, granules, capsules, elixirs, suspensions and the like. The compositions may be prepared by conventional means.

The (R) isomer of formula XIII may be formulated into such pharmaceutical compositions containing an amount of said isomer that is effective in treating multiple sclerosis, such compositions in unit dosage forms and such compositions comprising a solid pharmaceutically acceptable carrier.

Tablets and capsules containing the ingredients indicated below may be prepared by conventional techniques and are useful in treating multiple sclerosis when administered once a day.

| Ingredients | Weight (mg) | |
|---|---|---|
| | tablet | capsule |
| (R) isomer of formula XIII | 150 | 150 |
| tragacanth | 10 | — |
| lactose (spray-dried) | 197.5 | 250 |

-continued

| Ingredients | Weight (mg) | |
|---|---|---|
| | tablet | capsule |
| corn starch | 25 | — |
| talcum | 15 | — |
| magnesium stearate | 2.5 | — |
| Total | 400.0 | 400.0 |

The preferred pharmaceutical compositions from the standpoint of preparation and ease of administration are solid compositions, particularly liquid or hard-filled capsules and tablets containing from about 100 to 300 milligrams of the (R) isomer of formula XIII.

RESULTS

Employing the EAE method described above, the following results were obtained when the racemate, i.e., the compound of Example 5 of U.S. Pat. No. 4,673,672, and the corresponding (R) isomer of formula XIII and (S) isomer of formula VII were administered at 25 mg/kg/day over a period of 14 days.

| Compound | Animals with total paralysis | | Animals with EAE | |
|---|---|---|---|---|
| | No./total | % | No./total | % |
| control | 33/40 | 83 | 40/40 | 100 |
| Ex. 5 of U.S. Pat. No. 4,673,672 | 3/7 | 43 | 4/7 | 57 |
| (R) isomer of formula XIII | 2/7 | 29 | 2/7 | 29 |
| (S) isomer of formula VII | 6/7 | 86 | 7/7 | 100 |

As can be seen from the above results, the (S) isomer of formula VII appears to be devoid of any usefulness in treating multiple sclerosis upon administration of 25 mg/kg of said isomer in the above method. Moreover, it can be seen that the (R) isomer of formula XIII is more effective in treating multiple sclerosis than is the racemic mixture, i.e., Example 5 of U.S. Pat. No. 4,673,672.

Moreover, it has been discovered that the specific isomer prepared in Step 5 or Reaction D, i.e., the (S) isomer of formula VII, is more effective than the racemic mixture, i.e., Example 5 of U.S. Pat. No. 4,673,672, and the corresponding (R) isomer prepared in Step F or Step EE, i.e., the compound of formula XIII in treating tumors in vivo. The ability of the (S) isomer of formula VII to inhibit the growth of various lymphomas, sarcomas, myelomas and leukemia cell lines may be demonstrated employing the Tumor Cell Cytotoxity test (TCC test) as follows:

In flat bottom microtiter plates (Nunc Roskieide, Denmark) were placed Abelson 8.1 lymphoma, YAC-1, L1210 or P815 tumor cells in DMEM+10% fetal calf serum and the tumor cell-containing plates were incubated with 1, 3 and 5 μg of the test compound for a period of 6 to 72 hours. The number of viable tumor cells present in the Abelson 8.1, YAC-1, L1210 and P815 assays was determined by measuring the alkaline phosphatase in the following manner. The tumor cell plates were centrifuged (500×g) for ten minutes and the supernatant flicked off. Without further washing, 100 μl of buffer containing 20 μl of diethanolamine, 2 μM of $MgCl_2.6H_2O$, 2.5 μM of p-nitrophenylphosphate and 10 mg Triton X-100 were added. The samples were incubated for 60 minutes at room temperature and the enzymatic reaction was terminated by the addition of 100 μl of 0.5N NaOH. The absorbance was then measured at 405 nM using a Titertek Multiskan apparatus.

At an incubation period of 72 hours, the following results were obtained.

| Compound | Conc. (μg/ml) | % Inhibition | | | |
|---|---|---|---|---|---|
| | | Abelson 8.1 | YAC-1 | L1210 | P815 |
| Ex. 5 of U.S. Pat. No. 4,673,672 | 1 | 68 | 19 | 0 | 40 |
| | 3 | 97.4 | 74 | 80 | 87 |
| | 5 | 98.0 | 91.1 | 91.4 | 94.7 |
| (S) isomer of formula VII | 1 | 91.4 | 40 | 45 | 84 |
| | 3 | 97.9 | 78 | 92.3 | 93 |
| | 5 | 98.2 | 91 | 96.8 | 97.4 |
| (R) isomer of formula XIII | 1 | 29 | 8 | 16 | 32 |
| | 3 | 93.2 | 86 | 76 | 80 |
| | 5 | 95.4 | 95.5 | 87 | 97.2 |

As can be seen from the above results, the (S) isomer of formula VII is more effective in treating tumors than is the racemic mixture, i.e., Example 5 of U.S. Pat. No. 4,673,672, are the (R) isomer of formula XIII. More particularly, the (S) isomer is more effective in inhibiting different types of tumors than is either the racemic mixture or the (R) isomer, especially at lower concentrations.

The anti-tumor activity of the (S) isomer of formula VII may also be demonstrated employing the Influence on Cytotoxity of ET-18-OCH$_3$ test (IC-ET test) as follows:

Bone marrow cell macrophages (10$^5$/well) obtained from [BALB/CX57/BL$_6$]F1 mice were incubated with 10 μg of (±)-1-octadecyl-2-methoxy-3-phosphoryl choline (ET-18-OCH$_3$) for 24 hours in flat bottom microtiter plates (Nunc Roskieide, Denmark), after which time they are centrifuged and washed once. Abelson 8.1 lymphoma, YAC-1, L1210 or P815 tumor cells in DMEM+10% fetal calf serum and 1, 3 and 5 μg of the test compound were then added to the plates. With the cytotoxicity of ET-18-OCH (10 μg) alone set at 100%, the inhibition or enhancement of the cytotoxic effect, as measured by an alkaline phosphatase assay, was determined and values recorded after 72 hours for 1, 3 and 5 μg of the test substance. The following results were obtained:

| Compound | Conc. (μg/ml) | % Enhancement | | | |
|---|---|---|---|---|---|
| | | Abelson 8.1 | YAC-1 | L1210 | P815 |
| Ex. 5 of U.S. Pat. No. 4,673,672 | 1 | 99.6 | 84 | 90.6 | 96.6 |
| | 3 | 99.8 | 97.5 | 98.4 | 99.3 |
| | 5 | 99.9 | 98.8 | 99.1 | 99.4 |
| (S) isomer of formula VII | 1 | 99.5 | 89 | 96.6 | 97.6 |
| | 3 | 99.7 | 97.7 | 99.4 | 98.9 |
| | 5 | 99.8 | 99.1 | 99.8 | 99.7 |
| (R) isomer of formula XIII | 1 | 99.2 | 89 | 94.7 | 96.9 |
| | 3 | 99.7 | 98.4 | 98.6 | 98.2 |
| | 5 | 99.6 | 99.1 | 98.9 | 98.7 |

As can be seen from the above results, the (S) isomer of formula VII is somewhat more effective in enhancing the cytotoxic effect of ET-18-OCH$_3$ in different types of tumors than is the racemic mixture, i.e., Example 5 of U.S. Pat. No. 4,673,672, or the (R) isomer of formula XIII.

The usefulness of the (S) isomer of formula VII in treating tumors may additionally be demonstrated employing the following procedure:

Meth A fibrosarcoma cells were induced in BALB/C mice by administering methylcholanthrene according to the procedure of Old, et al (L. J. Old, E. A. Boyse, D. A. Clarke, and E. Carswell, Ann. N.Y. Acad. Sci., 101, 80 (1962). These tumor cells were harvested from the peritoneal cavity 10 to 12 days after administration of methylcholanthrene. Ten CBF mice of 10–12 week age were each implanted with 7.3×10$^6$ Meth A sarcoma cells to serve as control. A second group of ten CBF$_1$ mice were each implanted with 7.3×10$^6$ Meth A sarcoma cells and on day one after implant each mouse was treated p.o. with 5–50 μg of the test compound per day for a total of twenty or twenty-seven days. Tumor growth and survivors are assayed on days 7, 14, 21 and 28 after tumor implantation. Under these conditions, the following results were obtained:

| compound | conc. (μg/mouse) | Tumor Volume % of control | | | | Survivors (tumor-free) |
|---|---|---|---|---|---|---|
| | | Day 7 | Day 14 | Day 21 | Day 28 | |
| Ex. 5 of U.S. Pat. No. 4,673,672 | 5 | 82 | 47 | 20 | 32 | 3/10 |
| | 50 | 76 | 38 | 14 | 21 | 6/10 |
| (S) isomer of formula VII | 5 | 66 | 19 | 6 | 11 | 8/10 |
| | 50 | 70 | 28 | 8 | 13 | 8/10 |
| (R) isomer of formula XIII | 5 | 90 | 52 | 21 | 37 | 2/10 |
| | 50 | 85 | 53 | 21 | 32 | 3/10 |

As can be seen from the above results, the (S) isomer of formula VII is more effective in treating tumors than is the racemic mixture, i.e., Example 5 of U.S. Pat. No. 4,673,672, or the (R) isomer of formula XIII, especially at the lower dose. Moreover, whereas none of the control group animals survived, 8 out of 10 animals which were administered 5 μg of the (S) isomer survived.

In short, in view of the fact that the (S) isomer of formula VII is more effective in treating tumors than is the racemic mixture, i.e., Example 5 of U.S. Pat. No. 4,673,672, it can be concluded that pharmaceutical compositions comprising the (S) isomer of formula VII, as the active ingredient, offer a therapeutic advantage over known pharmaceutical compositions comprising the racemic mixture.

As with the multiple sclerosis use regarding the (R) isomer of formula XIII, the precise dosage of the (S) isomer of formula VII to be employed for inhibiting tumors depends upon several factors including the host, the nature and the severity of the condition being treated, the mode of administration and the particular compound employed. However, in general, satisfactory inhibition of tumors is achieved when the (S) isomer of formula VII is administered enterally, preferably orally, or parenterally, e.g., intravenously, at a daily dosage of 1–100 mg/kg, preferably 2–50 mg/kg body weight or, for most larger primates, at a total daily dosage of 50–1000 mg, preferably 100–700 mg. A typical oral daily dosage for most larger primates is 400 mg, or 10 mg/kg intravenously over a 24 hour period.

For most larger primates, a typical dosage unit for oral administration two to four times a day in the inhibition of tumors may contain 75 to 300 mg of the (S) isomer of formula VII. Preferred oral dosage units for inhibition of tumors contain 75 to 250 mg, especially 100 to 200 mg of the (S) isomer of formula VII.

Moreover, and as was the case with the multiple sclerosis use regarding the (R) isomer of formula XIII, the upper limit of dosage of the (S) isomer of formula VII for treating tumors is that imposed by side effects and can be determined by trial for the host being treated, including humans. Furthermore, the (S) isomer of formula VII may be combined with one or more pharmaceutically acceptable carriers and administered orally in the form of tablets, dispersible powders, granules, capsules, elixirs and suspensions.

The (S) isomer of formula VII may be formulated into such pharmaceutical compositions containing an amount of said isomer that is effective in treating tumors, such compositions in unit dosage forms and such compositions comprising a solid pharmaceutically acceptable carrier.

The following tablets and capsules may be prepared by conventional techniques and are useful as tumor inhibitors. The tablet may be administered two to four times a day whereas the capsule is suitably administered two or three times a day.

| Ingredients | Weight (mg) | |
|---|---|---|
| | Tablet | Capsule |
| (S) isomer of formula VII | 150 | 150 |
| tragacanth | 10 | — |
| lactose (spray-dried) | 197.5 | 250 |
| corn starch | 25 | — |
| talcum | 15 | — |
| magnesium stearate | 2.5 | — |
| TOTAL | 400.0 | 400 |

The preferred pharmaceutical compositions for tumor inhibition are solid compositions containing from 100 to 200 mg of the (S) isomer of formula VII.

The following examples are for the purposes of illustration only and are not intended in any way to limit the scope of the invention.

EXAMPLE 1

The following describes the synthesis of the (R) stereoisomer of 2,2-bis(hydroxymethyl)-tetrahydrofuran, monobutyrate employing the lipase PPL.

Preparation of 2,2-bis(hydroxymethyl)-tetrahydrofuran, dibutyrate

Into a two-neck, round bottom flask (equipped with an addition funnel, a reflux condenser and an outlet to an HCl trap) containing 101.6 g (0.77 mol) of 2,2-bis(hydroxymethyl)-tetrahydrofuran in 800 ml of dichloromethane, 176 ml of butyryl chloride was added (slightly exothermic) over a period of 40 minutes. The resultant solution (hydrogen chloride gas was quenched), was stirred for 21 hours, followed by the addition of 1200 ml of an aqueous sodium bicarbonate solution over a period of 30 minutes. The phases were separated and the aqueous phase was extracted three times with dichloromethane. The organic phases were combined, dried over magnesium sulfate, filtered and concentrated in vacuo. The resultant yellow residue was distilled to yield the dibutyrate compound as a colorless liquid (b.p. 127°–128° at 0.4 mmHg).

Preparation of-the (R) stereoisomer of 2,2-bis(hydroxymethyl)-tetrahydrofuran, monobutyrate 1.36 g (5 mmol) of the diester compound prepared in a) above was suspended in a buffered mixture comprising 50 ml of water and 50 ml of hexane, and the pH of the resultant suspension was adjusted to 7 by adding acetic acid and/or 2N sodium hydroxide. To the resultant buffered suspension was added, with stirring, 100 mg of the lipase PPL (porcine pancreas, commercially available from Sigma Chem Corp.-42 U/mg), which resulted in an immediate reaction. The reaction was allowed to proceed while the pH was continually adjusted to 7 by the addition of 2N sodium hydroxide. After the reaction slowed down (~45 minutes), the phases were separated and the aqueous phase was extracted three times at with ethyl acetate. The organic phases were then combined, dried over magnesium sulfate, filtered and concentrated in vacuo to yield the crude product. Flash chromatography on silica gel employing a mixture of hexane and ethyl acetate in a ratio of 1:1 as the eluent and Kugelrohr distillation yielded the desired (R) stereoisomer as an oil in a yield of 89%, a purity of 99% and displaying an optical rotation in toluene of $[\alpha]_{25}^D = +19.5°$.

EXAMPLE 2

The following describes the synthesis of the (R) stereoisomer of 2,2-bis(hydroxymethyl)-tetrahydrofuran, monobutyrate employing the microbial lipase LMJ.

1.36 g (5 mmol) of the diester compound prepared in Example 1a) above was suspended in 50 ml of buffer, and the pH of the resultant suspension was adjusted to 7 by adding acetic acid and/or 2N sodium hydroxide. To the resultant buffered suspension was added, with stirring, 19 mg of the microbial lipase LMJ (mucor javanicus, commercially available form Fluka Chem Co.-5 U/g). The reaction was allowed to proceed while the pH was continually adjusted to 7 by the addition of 2N sodium hydroxide. After ~5½ hours, the mixture was extracted three times with ethyl acetate. The organic phases were then combined, dried over magnesium sulfate, filtered and concentrated in vacuo to yield the crude product. Flash chromatography on silica gel employing a mixture of hexane and ethyl acetate in a ratio of 1:1 as the eluent and Kugelrohr distillation yielded the desired (R) stereoisomer as an oil in a yield of 64% and displaying an optical rotation in toluene of $[\alpha]_{25}^D = +14.3°$.

EXAMPLE 3

The following describes the synthesis of the more stable silylated form of the (R) stereoisomer of 2,2-bis(hydroxymethyl)-tetrahydrofuran, monobutyrate.

6.06 g (30 mmol) of the crude form of the compound of Example 1 was dissolved in 75 ml of dimethylformamide and to the solution was added 4.08 g (60 mmol) of imidazole and 12.38 g (45 mmol) of t-butylchlorodiphenyl silane. The resultant solution was then stirred at room temperature until no starting material was detectable (~3 to 12 hours.) 75 ml of water was then added and the resultant mixture was extracted four times with diethyl ether. The organic phases were then combined, washed with 100 ml of water, dried over magnesium sulfate, filtered and concentrated in vacuo. MPLC (medium pressure liquid chromatography) on silica gel employing a mixture of hexane and ethyl acetate in a ratio 9:1 as the eluent yielded the desired silyl ether as an oil.

EXAMPLE 4

The following describes the synthesis of the more stable tritylated form of the (R) stereoisomer of 2,2-bis(hydroxymethyl)-tetrahydrofuran, monobutyrate.

a) Preparation of the (R) stereoisomer of 2,2-bis(hydroxymethyl)-tetrahydrofuran, monobutyrate Into a 3-liter flask equipped with a stirrer, pH meter probe and auto-buret was added 1 liter of pH7 buffer, 1 liter of hexane and 2.2 g of the lipase PPL, after which time the pH of the resultant suspension was adjusted to 7 by adding acetic acid. To the resultant suspension was added with stirring, 27.2 g (100 mmol) of 2,2-bis(hydroxymethyl)-tetrahydrofuran, dibutyrate (diluted with minimum amount of hexane). The reaction was allowed to proceed while the pH was continually adjusted to 7 by the addition of 2N sodium hydroxide. After the reaction was ~98% complete, the reaction mixture was poured into 1 liter of ethyl acetate and extracted. The organic layer was separated, dried over sodium sulfate, filtered through silica gel, and evaporated to yield the desired product in crude form as an oil (>99% purity; optical rotation in toluene $[\alpha]_D^{25} = +19.5°$; b.p. 125° C. at 0.5 mmHg employing bulb to bulb distillation).

Preparation of the (R) isomer of a) in tritylated form 21.5 g (100 mmol) of the compound prepared in a) above, was dissolved in 400 ml of methylene chloride and the resultant solution was cooled to −30° C. To the cooled solution was added 10.51 ml (130 mmol) of pyridine and a solution of 33.454 g (120 mmol) of triphenylchloromethane in 100 ml of methylene chloride, while maintaining the temperature at −30° C. The reaction mixture was then allowed to warm slowly overnight to room temperature, after which time it was diluted with 400 ml of ethyl acetate, washed two times with 2N hydrochloric acid, and washed two times with saturated sodium chloride solution. The organic layer was then dried over sodium sulfate, filtered and the solvents were removed to yield the desired trityl ether in crude form.

EXAMPLE 5

The following describes the preparation of the (S) isomer of formula VII.

a) Preparation of 2-hydroxymethyl-2-trityloxymethyl-tetrahydrofuran (the (S) isomer of formula XIV)

48.82 g (110 mmol) of the compound of Example 4, 3.2 g of potassium carbonate and 500 ml of methanol were stirred at room temperature overnight, after which time the reaction mixture was diluted with 400 ml of ethyl acetate and washed with saturated ammonium chloride solution. The aqueous layer was then separated and extracted three times with ethyl acetate. The ethyl acetate layers were combined and washed two times with saturated sodium chloride solution, dried over sodium sulfate and filtered. The solvent was then removed and the crude product was chromatographed on silica gel, first employing an eluent mixture of ethyl acetate and hexane in a 1:3 ratio, and then employing an eluent mixture of ethyl acetate and hexane in a 1:1 ratio to yield the desired (S) isomer of formula XIV (m.p. 75.2°–77.6° C.; optical rotation in methanol $[a]_D^{25} = -3.85°$).

b) Preparation of 2-octadecyloxymethyl-2-trityloxymethyl-tetrahydrofuran (the (S) isomer of formula XV)

A mixture of 4.98 g (124.6 mmol) of sodium hydride (60% dispersion), 3.524 g (9.54 mmol) of tetrabutylammonium iodide and 105 ml of tetrahydrofuran was cooled to 5° C. under a nitrogen atmosphere. To the cooled mixture was then added a solution of 27.446 g (73.3 mmol) of the compound prepared in c) above in 105 ml of tetrahydrofuran and the resultant mixture was warmed to room temperature and stirred for twenty minutes. A solution of 29.322 g (87.9 mmol) of 1-bromooctadecane in 105 ml of tetrahydrofuran was then added and the reaction mixture was then heated to the reflux temperature and stirred overnight. The reaction mixture was then cooled to 5° C. and quenched with 50 ml of isopropanol, after which time 500 ml of a saturated ammonium chloride solution was added. The organic layer was then separated and washed two times with saturated sodium chloride solution, dried over sodium sulfate, filtered and concentrated to remove the solvent. The crude product was then chromatographed on silica gel, first employing hexane as the eluent, and then employing an eluent mixture of ethyl acetate and hexane in a 1:6 ratio to yield the desired (S) isomer of formula c) Preparation of 2-hydroxymethyl-2-octadecyloxymethyl-tetrahydrofuran (the (R) isomer of formula XVI)

To a stirred solution of 26.658 g (642.5 mmol) of the compound prepared in b) above and 500 ml of methylene chloride was added a precooled solution of 73.5 ml (954 mmol) of trifluoroacetic acid in 230 ml of water and the resultant solution was stirred at room temperature overnight. The organic layer was then separated, washed two times with saturated sodium bicarbonate solution, washed two times with saturated sodium chloride solution, dried over sodium sulfate, filtered and concentrated to remove the solvent. The crude product was then chromatographed on silica gel employing an eluent mixture of ethyl acetate and hexane in a 1:3 ratio to yield the desired (R) isomer of formula XVI.

Preparation of the (S) isomer of formula VII

To a 500 ml, 4-neck, round bottom flask is added 10.042 g (26.1 mmol) of the compound prepared in c) above and 200 ml of methylene chloride, and the resultant solution was cooled to 3° C. under a nitrogen atmosphere. To the cooled solution was added 2.57 ml (27.6 mmol) of phosphorus oxychloride, after which time 4.57 ml (32.8 mmol) of triethylamine was added, dropwise, while the temperature was maintained at below 5° C. The resultant mixture was then stirred at room temperature for 20 hours and cooled to 5° C. To the cooled mixture was then added 22.8 ml (281.5 mmol) of pyridine, 0.296 g (2.42 mmol) of 4-dimethylaminopyridine and 13.897 g (50.5 mmol) of Choline reagent. The reaction mixture was then stirred at room temperature for 72 hours, the solids were removed by filtration, and the mixture was concentrated to remove the solvents. The resultant residue was then dissolved in a mixture of 205 ml of tetrahydrofuran, 48 ml of water and 25 ml of pyridine, and the resultant solution was heated to the reflux temperature and maintained at the reflux temperature for 5 hours. The solution was then cooled to room temperature, filtered through a column of 685 g of Amberlite MB-3 ion exchange resin, and eluted with a mixture of 10% water in tetrahydrofuran. The fractions containing the desired product were then collected, combined and concentrated and the resultant residue was cooled to 0° C. 170 ml of acetone was then added, dropwise, and the resultant suspension was stirred at 0°

C. for 30 minutes, after which time a yellow waxy solid was collected by filtration. The solid was then chromatographed on silica gel, first employing an eluent mixture of methylene chloride, methanol and water in a ratio of 79:19:2, and then employing an eluent mixture of methylene chloride, methanol and water in a ratio of 10:5:1. The fractions were then combined, concentrated to a volume of 40 ml and cooled to 5° C. 160 ml acetone was then added, dropwise, and a white precipitate formed. The mixture was then stirred at 5° C. for 30 minutes and the solid was collected by filtration and then dissolved in 250 ml of absolute ethanol. After 200 ml of the solvent was removed, the remainder was added, dropwise, to 260 ml of acetone. 1.2 ml of water was then added and the mixture was cooled to 5° C. and maintained at this temperature overnight. The resultant solid was collected by filtration, washed with cold acetone and dried-on a high vacuum pump at room temperature to yield the desired (S) isomer of formula VII (m.p. 188° C.; optical rotation in ethanol $[\alpha]_D^{25} = -1.9°$).

EXAMPLE 6

The following describes the preparation of the (R) isomer of formula XIII.

a) Preparation of 2-benzyloxymethyl-2-trityloxymethyl-tetrahydrofuran (the (S) isomer of formula XVII)

A mixture of 9.857 g (246.4 mmol) of sodium hydride (60% dispersion), 6.91 g (18.8 mmol) of tetrabutylammonium iodide and 205 ml of tetrahydrofuran was cooled to 5° C. To the cooled mixture was then added a solution of 54.284 g (144.96 mmol) of the compound of Example 5a) in 205 ml of tetrahydrofuran, and the resultant mixture was warmed to room temperature and stirred for 15 minutes. A solution of 20.7 ml (173.9 mmol) of benzyl bromide in 245 ml of tetrahydrofuran was then added and the reaction mixture was heated to reflux and maintained at this temperature, with stirring, for 2½ hours. The reaction mixture was then cooled to 10° C. and quenched with 45 ml of isopropyl alcohol. 900 ml of a saturated ammonium chloride solution was then added, and the organic layer was separated and washed with saturated sodium chloride solution, dried over sodium sulfate, filtered and concentrated to remove the solvent. The crude product was then chromatographed on silica gel employing an eluent mixture of hexane and ethyl acetate in a 95.5 ratio to yield the desired (S) isomer of formula XVII.

b) Preparation of 2-benzyloxymethyl-2-hydroxymethyl-tetrahydrofuran (the (R) isomer of formula XVIII)

To a stirred solution of 64.719 g (139.5 mmol) of the compound prepared in a) above and 1600 ml of methylene chloride was added a precooled solution of 240 ml (3.11 moles) of trifluoroacetic acid in 750 ml of water, and the resultant solution was stirred at room temperature overnight. The organic layer was then separated, washed two times with saturated sodium bicarbonate solution, washed two times with saturated sodium chloride solution, dried over sodium sulfate, filtered and concentrated to remove the solvent. The crude product was then chromatographed on silica gel, first employing an eluent mixture of ethyl acetate and hexane in a 1:2 ratio, and then employing an eluent mixture of ethyl acetate and hexane in a 3:2 ratio to yield the desired. (R) isomer of formula XVIII.

c) Preparation of 2-benzyloxymethyl-2-octadecyloxymethyl-tetrahydrofuran (the (R) isomer of formula XIX)

A mixture of 6.764 g (169.1 mmol) of sodium hydride (60% dispersion), 4.775 g (12.9 mmol) of tetrabutylammonium iodide and 130 ml of tetrahydrofuran was cooled to 5° C. under a nitrogen atmosphere. To the cooled mixture was then added a solution of 22.11 g (99.5 mmol) of the compound prepared in b) above in 130 ml of tetrahydrofuran, and the resultant mixture was warmed to room temperature and stirred for 20 minutes. A solution of 39.794 g (119.4 mmol) of 1-bromooctadecane in 155 ml of tetrahydrofuran was then added and the reaction mixture was then heated to the reflux temperature and stirred overnight. The reaction mixture was then cooled to 5° C. and quenched with 50 ml of isopropanol, after which time 500 ml of a saturated ammonium chloride solution was added. The organic layer was then separated and washed two times with saturated sodium chloride solution, dried over sodium sulfate, filtered and concentrated to remove the solvent. The crude product was then chromatographed on silica gel, first employing hexane as the eluent, and then employing an eluent mixture of ethyl acetate and hexane in a 1:6 ratio to yield the desired (R) isomer of formula XIX.

d) Preparation of 2-hydroxymethyl-2-octadecyl-oxymethyl-tetrahydrofuran (the (S) isomer of formula XX)

To a Parr bottle was added 11.5 g of 10% palladium on carbon and a solution of 22.523 g (47.4 mmol) of the compound prepared in c) above in 250 ml of a 95% ethanol/water mixture. 10 drops of acetic acid was then added and the mixture was hydrogenated at room temperature under a pressure of 48 lbs. of hydrogen until uptake was complete. The catalyst was then filtered off and the filtrate was concentrated in vacuo. The residue was then chromatographed on silica gel employing an eluent mixture of ethyl acetate and hexane in a 1:3 ratio to yield the desired (S) isomer of formula XX.

Preparation of the (R) isomer of formula XIII

Following essentially the last step of the procedure in preparing the compound of Example 5, and using in place of the compound prepared in Example 5c) an equivalent amount of the compound prepared in d) above, the (R) isomer of formula XIII was obtained (m.p. 193° C.; optical rotation in ethanol $[\alpha]_D^{25} = +1.9°$).

What is claimed is:

1. A method of treating multiple sclerosis comprising administering to a subject in need of such treatment a therapeutically effective amount of the (R) isomer of 2-[(2-octadecyloxymethyl-tetrahydro-2-furanylmethoxy)-hydroxyphosphinyloxy]-N,N,N-trimethylethanaminium hydroxide inner salt-4-oxide having the formula

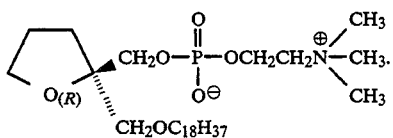

2. A method according to claim 1 wherein the (R) isomer is administered at a daily dosage of between 0.5 and 30 mg/kg body weight.

3. A method according to claim 2 wherein the (R) isomer is administered at a daily dosage of between 1 and 20 mg/kg body weight.

4. A method according to claim 1 wherein the (R) isomer is administered at a daily dosage of between 100 and 600 mg.

5. A method according to claim 4 wherein the (R) isomer is administered at a daily dosage of between 100 and 300 mg.

* * * * *